United States Patent
Al-Assaf et al.

(10) Patent No.: US 7,462,710 B2
(45) Date of Patent: Dec. 9, 2008

(54) MODIFIED GUM ARABIC

(75) Inventors: Saphwan Al-Assaf, Wrexham (GB); Glyn Owen Phillips, London (GB); Yasushi Sasaki, Toyonaka (JP); Tsuyoshi Katayama, Toyonaka (JP)

(73) Assignees: Phillip Hydro Colloids Research Limited, London (GB); San-Ei Gen F.F.I., Inc., Osaka (JP)

( * ) Notice: Subject to any disclaimer, the term of this patent is extended or adjusted under 35 U.S.C. 154(b) by 0 days.

(21) Appl. No.: 10/498,988

(22) PCT Filed: Apr. 7, 2004

(86) PCT No.: PCT/JP2004/005050

§ 371 (c)(1), (2), (4) Date: Feb. 10, 2005

(87) PCT Pub. No.: WO2004/089991

PCT Pub. Date: Oct. 21, 2004

(65) Prior Publication Data

US 2005/0124805 A1    Jun. 9, 2005

(30) Foreign Application Priority Data

Apr. 7, 2003   (JP) ............................ 2003-103495

(51) Int. Cl.
- C08B 37/00 (2006.01)
- C12P 19/04 (2006.01)
- A61K 31/715 (2006.01)
- A61K 47/04 (2006.01)

(52) U.S. Cl. .................. 536/114; 536/123; 536/124; 514/54; 514/937

(58) Field of Classification Search ................ 536/114, 536/123, 124; 514/54
See application file for complete search history.

(56) References Cited

U.S. PATENT DOCUMENTS 5,646,029 A * 7/1997 Chen et al. ................... 435/419

FOREIGN PATENT DOCUMENTS

| JP | 58-183701 | 10/1983 |
| JP | 02-49001 | 2/1990 |

(Continued)

OTHER PUBLICATIONS

P.A. Williams et al; "Gum arabic"; *Handbook of Hydrocolloids*; (2000); pp. 155-168.

(Continued)

*Primary Examiner*—Shaojia Anna Jiang
*Assistant Examiner*—Everett White
(74) *Attorney, Agent, or Firm*—Galvin & Palmer

(57) ABSTRACT

The present invention provides a water-soluble modified gum arabic with a weight average molecular weight not less than 0.9 million and arabinogalactan protein not less than 17% by weight obtained by heating Acacia Senegal gum arabic and modified water-soluble gum arabic with a weight average molecular weight not less than 2.5 million and with protein containing high molecular weight components of not less than 25% by weight. Moreover, the present invention provides modified gum arabic with standardized and predictable molecular properties and methods for providing the modified gum arabic endowed with high emulsification efficiency and stability and for uniforming natural variations in unmodified gum arabic. The present invention changes the natural protein distribution of gum arabic, and increases AGP content.

11 Claims, 5 Drawing Sheets

FOREIGN PATENT DOCUMENTS

| | | | |
|---|---|---|---|
| JP | 2000-166489 | | 6/2000 |
| JP | 2000166489 A | * | 6/2000 |
| WO | WO02/072862 A2 | | 9/2002 |

OTHER PUBLICATIONS

M.I. Thurston et al; "Effect of Heat an pH on the Carbohydrate Epitopes of Gum from *Acacia senegal* Recognised by Monoclonal Antibodies"; *Food and Agricultural Immunology* (1999) 11; pp. 145-153.

M.I. Thurston et al; "Detection of Gum from *Acacia seyal* and Species of Combretum in Admixtures with *A. senegal* Using Monoclonal Antibodies"; *Food and Agricultural Immunology* (1998) 10; pp. 237-247.

O.H.M. Idris et al; "Characterization of gum from *Acacia senegal* trees of different age and location using multidetection gel permeation chromatography;" *Food Hydrocolloids* (1998) 12, pp. 379-388.

Mohamed E. Osman et al; "The molecular characterization of the polysaccharide gum from *Acacia sendegal*"; *Carbohydrate Research* (1993) 246, pp. 303-318.

Mikio Nakamura et al; "Effect of Molecular Weight of Gum Arabic on Stability of Emulsion"; JP Pharmaceuticals (1982) vol. 42, No. 1; pp. 25-29.

Martin Glicksman et al; "Gum Arabic"; *Industrial Gums—Polysaccharides and Their Derivatives* $2^{nd}$; (1973) pp. 197-263.

Martin Glicksman; "Natural Plant Exudates"; *Gum Technology in the Food Industry*; (1969); pp. 94-124.

* cited by examiner

MODIFIED GUM ARABIC

TECHNICAL FIELD

The present invention relates to modified gum arabic. In particular, the invention relates to modified gum arabic wherein the properties such as emulsifiability, emulsion stability, encapsulation ability, adhesiveness, protective colloid property and filmforming ability have been improved or enhanced compared to natural gum arabic. Specifically, the invention relates to the modified gum arabic obtained from gum arabic belonging to the *Acacia senegal* species, the modified gum arabic comprising components with specific molecular weight and having a protein distribution that are suitable for uniformly providing superior emulsifiability.

BACKGROUND ART

Gum arabic is a natural exudate from the trunks and branches of the plants that belong to the genus Acacia (especially, *Acacia senegal* and *Acacia seyal*) of the Leguminasae family. Gum arabic is highly soluble in water and its aqueous solution provides high emulsifiability, emulsion stability, encapsulation ability, adhesiveness, protective colloid property and filmforming ability even at low concentration, so that it has been widely used as an emulsifier, thickener, stabilizer, binder, and coating agent.

Gum arabic is collected in various countries in the Sahara region of Africa and has a wide variation in molecular weight and composition of constituent components due to differences in the soil and climate in each habitat and age of the original tree. For this reason, functions of gum arabic in its original state delivered from the habitat are nonuniformity, and thereby properties of preparation using the gum arabic are not consistent (Williams, P. A. and Phillips, G. O., (2000) in Handbook of Hydrocolloids, pp. 155-168, Editors: Williams, P. A. and Phillips, G. O., Woodhead, London and New York). In the present specification, such gum arabic is referred to as simply "gum arabic" or "natural gum arabic" or "unmodified gum arabic", as distinguished from "modified gum arabic" of the present invention.

As mentioned above, emulsifiability is one of the useful properties that gum arabic exhibits in a wide variety of products. Several methods have been proposed and studied to reduce as much as possible the variation of emulsifiability between samples attributable to the variation of the properties of natural gum arabic and to enhance emulsifiability. For instance, one method comprises removing metal ions from gum arabic to obtain arabic acid and subjecting it to thermal modification to improve its emulsifiability (Japanese Unexamined Patent Publication No. 1990-49001), and another method comprises modifying gum arabic having a loss-on-drying of not more than 50 weight % by heating it at 60-140° C. for not less than 30 minutes to thereby enhance its emulsifiability (Japanese Unexamined Patent Publication No. 2000-166489).

However, these methods do not satisfactorily modify gum arabic so as to obtain the expected emulsifiability. Therefore, effective methods for manufacturing a modifying gum arabic having uniform quality and improved emulsifiability are still required. Furthermore, it is necessary to develop a method for manufacturing modified gum arabic, which has improved properties, such as emulsion stability, encapsulation ability, adhesiveness, protective colloid property, or filmforming ability, as well as the above-mentioned emulsifiability, and has a uniform quality by being reduced variation between natural gum arabic samples.

Documents relating to gum arabic include the following Documents 1-4 can be listed, in addition to the aforesaid documents.

Document 1: Mikio Nakamura, Pharmaceutics, Vol. 42, No. 1 (1982) pp. 25-29.
Document 2: Carbohydrate Research, 246 (1993) pp. 303-318
Document 3: WO02/072862
Document 4: Japanese Unexamined Patent Publication No. 1983-18370

BRIEF DESCRIPTION OF THE DRAWINGS

FIG. 1(A) shows the chromatogram of Sample 1 (untreated: natural gum arabic).

DISCLOSURE OF THE INVENTION

Figure 1:
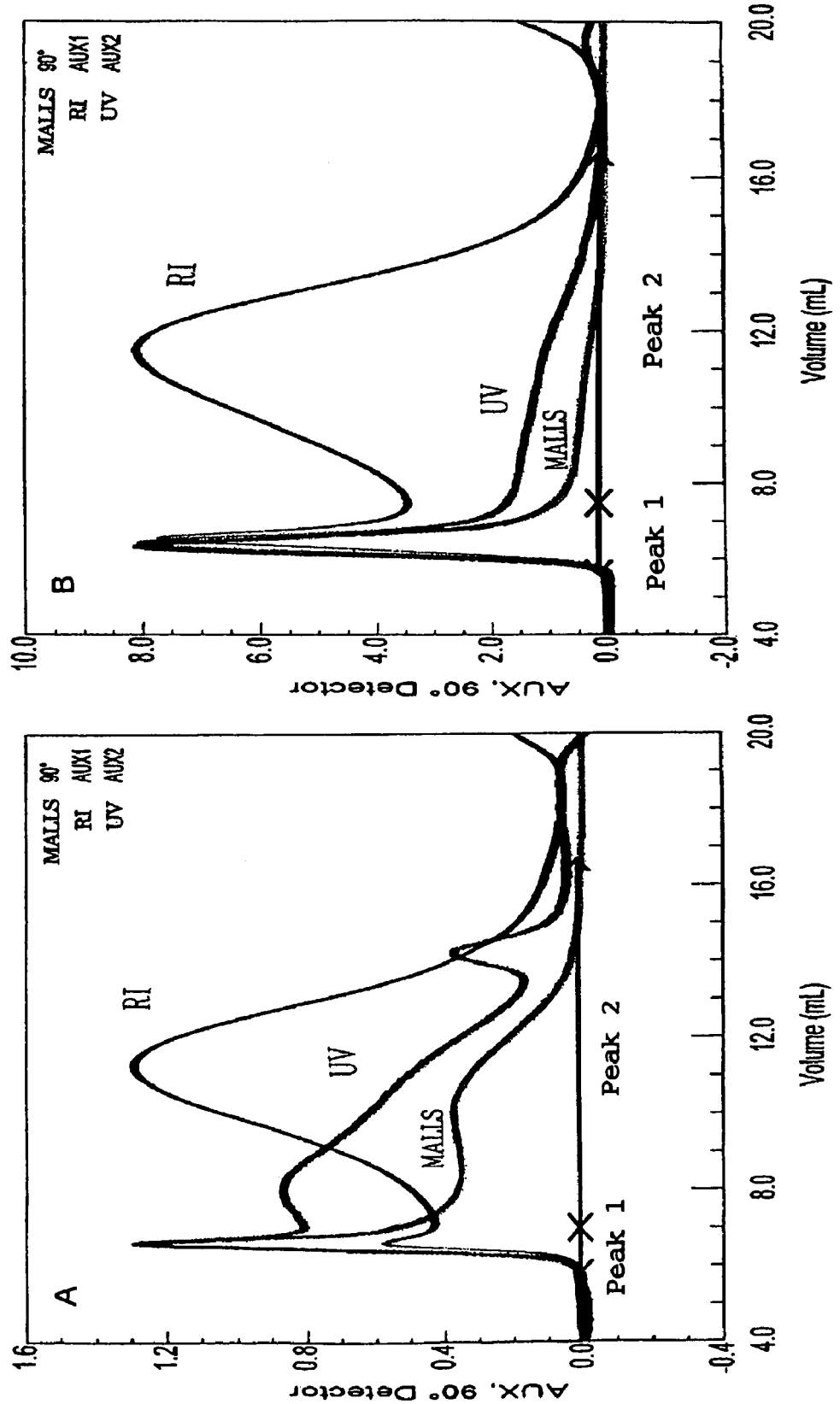
FIGS. 1(A) and (B) show chromatograms of Sample 1 and Sample 1/36 prepared in Experimental Example 1 obtained when these were subjected to GPC-MALLS mentioned in Experimental Example 1.
FIG. 1(B) shows the chromatogram of Sample 1/36 (heat-treated: modified gum arabic).

The first object of the present invention is providing modified gum arabic having a high emulsifiability, especially modified gum arabic having substantially uniform quality in emulsifiability. Furthermore, the invention aims to provide an emulsifier using such modified gum arabic.

The second object of the present invention is providing modified gum arabic wherein any one or more of the properties such as emulsifiability, emulsion stability, encapsulation ability, adhesiveness, protective colloid property and filmforming ability has been improved or enhanced compared to natural (unmodified) gum arabic.

The third object of the present invention is providing someone with safe modified gum arabic exhibiting the immunological reactivity the same as or similar to natural (unmodified) gum arabic.

The inventors of the present invention conducted extensive research to reach the above-mentioned objectives, and found that emulsifiability is improved by heating natural gum arabic (*Acacia senegal* or *Acacia seyal*) under specific conditions and that such modified gum arabic with improved emulsifiability is significantly different from natural gum arabic in at least one of weight average molecular weight and a protein distribution. The present invention has been accomplished based on the above findings, and comprises the following aspects.

Item 1. Water-soluble modified gum arabic having a weight average molecular weight of not less than 0.9 million that is obtained by heating gum arabic from *Acacia senegal*.

Item 2. Water-soluble modified gum arabic having the weight average molecular weight of not less than 1.5 million that is obtained by heating gum arabic from *Acacia senegal*.

Item 3. Water-soluble modified gum arabic having the weight average molecular weight of not less than 2 million that is obtained by heating gum arabic from *Acacia senegal*.

Item 4. Water-soluble modified gum arabic having an arabinogalactan protein content of not less than 17 weight % that is obtained by heating gum arabic from *Acacia senegal*.

Item 5. Water-soluble modified gum arabic having the weight average molecular weight of not less than 0.9 million and an arabinogalactan protein content of not less than 10 weight % that is obtained by heating gum arabic from *Acacia senegal*.

Item 6. Water-soluble modified gum arabic according to Items 1 to 5, wherein a difference in degree of immunological inhibition is within ±10% between the water-soluble modified gum arabic and unmodified gum arabic from *Acacia senegal* as measured by indirect competitive ELISA using a quantifiable antibody for gum arabic.

Item 7. Water-soluble modified gum arabic having a weight average molecular weight of not less than 2.5 million that is obtained by heating gum arabic from *Acacia seyal*.

Item 8. Water-soluble modified gum arabic having a protein-containing high molecular weight component content of not less than 25 weight % that is obtained by heating gum arabic from *Acacia seyal*.

Item 9. Water-soluble modified gum arabic having a weight average molecular weight of not less than 1.5 million and a protein-containing high molecular weight component content of not less than 22 weight % that is obtained by heating gum arabic from *Acacia seyal*.

Item 10. Water-soluble modified gum arabic according to any one of Items 7 to 9, wherein a difference in degree of immunological inhibition is within ±10% between the water-soluble modified gum arabic and unmodified gum arabic from *Acacia seyal* as measured by indirect competitive ELISA using a quantifiable antibody for gum arabic.

Item 11. Water-soluble modified gum arabic according to any one of Items 1 to 6, which is obtained by heating gum arabic from *Acacia senegal* at 110° C. for not less than 10 hours or under conditions capable of obtaining substantially same effect.

Item 12. Water-soluble modified gum arabic according to any one of Items 7 to 10, which is obtained by heating gum arabic from *Acacia seyal* at 110° C. for not less than 10 hours or under conditions capable of obtaining substantially same effect.

Item 13. A method for manufacturing the modified gum arabic of any one of Items 1 to 6, comprising a step of heating gum arabic from *Acacia senegal* at 110° C. for not less than 10 hours or under conditions capable of obtaining substantially same effect.

Item 14. A method for manufacturing the modified gum arabic of any one of Items 7 to 10, comprising a step of heating gum arabic from *Acacia seyal* at 110° C. for not less than 10 hours or under conditions capable of obtaining substantially same effect.

Item 15. An emulsifier comprising the modified gum arabic of any one of Items 1 to 10 as an active component.

Item 16. An emulsifier according to Item 15, comprising the modified gum arabic of any one of claims 1 and 4 as an active component.

Item 17. A novel emulsifier comprising the modified gum arabic as an active component that has a protein distribution different from that of natural gum arabic from *Acacia senegal* or *Acacia seyal* and a higher arabinogalactan protein content than that of natural gum arabic from *Acacia senegal* or *Acacia seyal*.

Item 18. An emulsion, which is obtained by dispersing and stabilizing a hydrophobic substance in a hydrophilic solvent using the emulsifier of Items 15 or 16.

Item 19. The emulsion according to Item 18, which is an O/W emulsion or a W/O/W emulsion.

Item 20. The emulsion according to Item 18, wherein the hydrophobic substance is an edible hydrophobic substance.

Item 21. The emulsion according to any one of Items 18 to 20, wherein the hydrophobic substance is at least one selected from the group consisting of essential oils, oleoresins, absolutes, oil-based flavorings, oil-based colorants, oil-soluble vitamins, $C_{18}$-$C_{22}$ polybasic unsaturated fatty acids, animal and vegetable fats and oils, SAIB and $C_6$-$C_{12}$ fatty-acid triglycerides.

Item 22. A method for preparing an emulsion comprising a step of dispersing a hydrophobic substance in a hydrophilic solvent using any emulsifier of Item 15.

Item 23. A thickener, coating agent, binder and material for capsules comprising the modified gum arabic according to any one of Items 1 to 10 as an active component.

Item 24. A use of the modified gum arabic according to any one of Items 1 to 10 for preparation of emulsifier.

Item 25. A use of the modified gum arabic according to any one of Items 1 to 10 for preparation of emulsion.

Item 25. A use of the modified gum arabic according to any one of Items 1 to 10 for preparation of a thickener, coating agent, binder and material for capsules.

As mentioned above, the present invention provides a modified gum arabic from the species *Acacia senegal* or *Acacia seyal* which is obtained by treating a natural gum arabic from the species *Acacia senegal* or *Acacia seyal*, respectively. These natural gum arabic from these species have different molecular weights, different protein distributions and have different properties, due to their structural differences. For instance, the natural gum arabic from *A. senegal* is laevorotatory and has the specific optical rotation of approximately −30 degrees. On the other hand, the natural gum arabic from *A. seyal* is dextrorotatory and has the specific optical rotation of approximately +50 degrees. Additionally, compared to the gum arabic from *A. senegal*, it is known that gum arabic from *A. seyal* has a lower protein nitrogen content (nitrogen content), a lower viscosity, and a different sugar composition.

BEST MODE FOR CARRYING OUT THE INVENTION (1) Modified Gum Arabic derived from *A. senegal*

(1-1) The present invention provides water-soluble modified gum arabic having a weight average molecular weight of not less than 0.9 million, preferably not less than 1.5 million, and more preferably not less than 2 million that is obtained by heating gum arabic from *Acacia senegal*.

The weight average molecular weight is determined by the use of a gel permeation chromatography wherein three detectors, i.e., a multi angle laser light scattering (MALLS) detector, a refractive index (RI) detector and an ultraviolet (UV)

detector are coupled by on-line. In the present specification, a technique of such gel permeation chromatography is referred to as "GPC-MALLS". According to the GPC-MALLS, the molecular weight is measured by the MALLS detector, the weight of each component (composition ratio) is measured by the RI detector, and protein content is measured by the UV detector. Therefore, it is possible to obtain the molecular weight and the composition of the analyzed components without reference to a standard gum arabic of known molecular weight. For detailed principals and characteristics of the GPC-MALLS, see Idris, O. H. M., Williams, P. A. Phillips, G. O.; Food Hydrocolloids, 12, (1998) pp. 375-388".

Conditions for GPC-MALLS employed in the present invention are as below:

Column: Superose=(6HR) 10/30 (Pharmacia Biotech, Sweden)
Flow rate: 0.5 ml/minute
Elution solvent: 0.2 M NaCl
Preparation of sample: The sample to be analyzed is diluted with the elution solvent (0.2 M NaCl).
Sample concentration: 0.4% (W/V)
Injection volume of sample solution: 100 µl
dn/dc: 0.141
Temperature: Room temperature
Detector: 1. MALLS (multi angle laser light scattering) detector: DAWN DSP (manufactured by Wyatt Technology Inc., USA), 2. RI detector, 3. UV detector (absorption at 214 nm)

By processing the data obtained by the GPC-MALLS conducted under the above-described conditions using software, i.e., ASTRA Version 4.5 (Wyatt Technology), each parameter of the components of the gum arabic such as the weight average molecular weight, recovery rate (% mass), polydispersity value (P) and root mean square radius of gyration (Rg) can be obtained. When the data is processed considering the whole peaks on the chromatogram obtained using an RI detector as one peak, the obtained molecular weight is identified as the weight average molecular weight ($M_{wt}$) of the present invention (specifically, "$M_{wt}$ processed as one peak"). When the point where the RI chart begins to rise from the baseline of the chromatogram is defined as the "starting point", and the point where the RI chart falls and intersects the baseline is defined as the "ending point", the aforementioned one peak on the chromatogram means the area from the starting point to the ending point.

There is no limitation to the weight average molecular weight of the modified gum arabic of the present invention as long as it is not less than 0.9 million, but preferably it is not less than 1.2 million, more preferably not less than 1.5 million, and still more preferably not less than 2 million. There is no specific upper limit to the weight average molecular weight as long as the modified gum arabic is soluble in water; however, it is preferably 2.5 million or less.

Furthermore, the modified gum arabic of the present invention is characterized in that it has the foresaid weight average molecular weight and is water-soluble. "Water-soluble" in this specification means that a sample is almost completely dissolved in an excess of water, regardless of the type of water, e.g., ion-exchanged water or ion-containing water, or water temperature as long as the gum arabic is soluble.

Hydrogelatinous gum arabic cannot be dissolved in water even if a large amount of water is added or by heating, and therefore the term "water-soluble" is used in the present specification to distinguish the modified gum arabic of the invention from hydrogelatinous gum arabic, which is insoluble in water. In other words, the modified gum arabic of the invention does not include modified polymeric gum: arabit that are insoluble in water, such as hydrogels, etc.

Moreover, it is preferable that the modified gum arabic of the present invention has the foresaid weight average molecular weight, be water-soluble, and be the same as or similar to unmodified gum arabic in terms of immunological reactivity. The phrase "the same as or similar to unmodified gum arabic in terms of immunological reactivity" means that difference between the degree of immunological inhibition of the modified gum arabic and that of unmodified gum arabic from *Acacia senegal* is within ±10%, as measured by indirect competitive ELISA using a quantifiable antibody for gum arabic, for example "SYCC7" [Thurston, M. I. et al., Detection of gum from *Acacia seyal* and species of combretum in mixtures with *A. senegal* using monoclonal antibodies, Food & Agric. Immunol., 10: 237-241(1998); Thurston, M. I. et al., Effect of heat and pH on carbohydrate epitopes from *Acacia senegal* by specific monoclonal antibodies, Food & Agric. Immunol., 11: 145-153(1999)].

The form of the modified gum arabic of the present invention is not limited and it can take any form including blocks, beads, coarse pulverizates, granules, pellets and powders.

The modified gum arabic of the present invention can be prepared by heating gum arabic from *Acacia senegal* using a thermostat or a heater, such as an oven, for example, at 110° C. for not less than 10 hours.

The unmodified gum arabic (*A. senegal*) used as a raw material in this embodiment is a natural exudate obtained from the trunks and branches of *Acacia senegal* of the genus *Acacia*, family Leguminasae or any other tree belonging to the same genus. It is also possible to use unmodified gum arabic that has been subjected to a treatment, such as purification treatment, desalting treatment, pulverization, or spray drying, etc.

The unmodified gum arabic (*A. senegal*) is produced in countries of North and West Africa from Ethiopia to Senegal (Ethiopia, Sudan, Senegal, Nigeria, Niger, and Ghana), countries of East Africa such as Kenya and Uganda, the Sahara region of Africa and the basins of the tributaries of the Nile. The unmodified gum arabic (*A. senegal*) produced in any of the above areas can be used in the present invention regardless of its origin.

Furthermore, unmodified gum arabic (*A. senegal*) is not particularly restricted in its water content. Commercially available unmodified gum arabic (*A. senegal*) undergoes a reduction in water content when dried by heating at 105° C. for 6 hours (loss on drying), generally not more than 40 weight %, preferably not more than 30 weight %, and more preferably not more than 20 weight %. In the present invention, unmodified gum arabic (*A. senegal*) having such water contents or showing a reduction in water content (loss-on-drying) can be used without limitation.

Unmodified gum arabic (*A. senegal*) can usually be procured in the forms of blocks, beads, coarse pulverizates, granules, pellets, and powders (including spray dried powder). However, in the present invention, unmodified gum arabic (*A. senegal*) of any form can be used without limitation as a raw material to be processed. It is possible to use spray dried gum arabic powder having an average particle diameter of several tens µm to several hundred µm. There is no particular upper limit to the average particle diameter but from the point of view of modification efficiency, the average particle diameter is preferably not more than 100 mm. The average particle diameter is preferably in the range from 1 mm to 100 mm and more preferably in the range from 2 mm to 50 mm.

Examples of the methods for heating unmodified gum arabic (*A. senegal*) include heating unmodified gum arabic at 110° C. for more than 10 hours using an oven (thermostat) as mentioned above. The preferable heat treatment is such that unmodified gum arabic (*A. senegal*) is heated at 110° C. for not less than 15 hours, more preferably for not less than 24 hours, and still more preferably for not less than 48 hours. While depending on the type of the unmodified gum arabic (*A. senegal*) to be subjected to heat treatment, the upper limit to the duration of heating when heated at 110° C. may be about 72 hours. As long as it is possible to obtain modified gum arabic that has the molecular weight specified in the present specification and that is soluble in water, the heating method is not limited to the above examples and heating temperature, duration of heating, heating means, and heating conditions (relative humidity, an opened or a closed system) can be optionally selected. The effects of the present invention achieved by the heat treatment conducted under the conditions described above can also be obtained by a method wherein unmodified gum arabic is heated at a temperature lower than 110° C. for more than 10 hours or at a temperature higher than 110° C. for a shorter time. Specifically, a method wherein the unmodified gum arabic is heated at 80° C. for 3 days to 1 week or longer may be mentioned as one example of the former case. When the unmodified gum arabic is heated using microwave radiation instead of an oven, the same effects can be achieved in less time. In addition, a heat treatment in the absence of oxygen, such as under nitrogen displacement conditions, is desirable because it can prevent discoloration of the gum arabic.

(1-2) The present invention also provides water-soluble modified gum arabic that contains not less than 17 weight % arabinogalactan protein that is obtained by heating gum arabic from *Acacia senegal*.

Arabinogalactan protein (hereinafter, simply described as "AGP") is one of three major components contained in gum arabic along with arabinogalactan (AG) and glycoprotein (GP). Unmodified gum arabic (*A. senegal*) generally contains AGP in a proportion of 5-15 weight %.

The content of AGP in gum arabic (unmodified gum arabic and modified gum arabic) can be determined by the SGPC-MALLS mentioned above. Specifically, when the RI Chart of a chromatogram obtained using an RI detector is divided into two parts, i.e., Peak 1 (high molecular weight fraction) which traces the first eluted portion, and Peak 2 (low molecular weight fraction) which traces the later eluted portion, and the data are then processed with ASTRA Version 4.5 (Wyatt Technology) software, the obtained recovery ratio of Peak 1 (% Mass) corresponds. to the AGP content (weight %) of the gum arabic. This is explained in detail with reference to the chromatogram (FIG. 1(A)) showing the results wherein unmodified gum arabic (*A. senegal*) was analyzed using the GPC-MALLS. In the RI chromatogram, the point where the RI chart begins to rise from the baseline of the chromatogram is defined as the "starting point" and the point where the RI chart falls and intercepts the base line is defined as the "ending point". Between the starting point and the ending point, the point where the RI value shows a minimum is defined as the boundary, with the area between the starting point and the boundary being defined as Peak 1 and the area between the boundary and the ending point being defined as Peak 2.

The content of AGP in modified gum arabic of the present invention is not specifically restricted as long as it is not less than 17 weight %, but preferably it is not less than 20 weight %. Its upper limit is not particularly restricted as long as the modified gum arabic is soluble in water but it is generally about 30 weight %.

The modified gum arabic obtained by the present invention is characterized in that is has an AGP content in the above-mentioned range and is soluble in water. Furthermore, it is preferable that the modified gum arabic of the present invention contains AGP in the ratio mentioned above, be water-soluble, and has properties the same as or similar to those of unmodified gum arabic in terms of immunological reactivity. "Water-soluble" and "properties the same as or similar to those of unmodified gum arabic in terms of immunological reactivity" described here have the same meanings as stated in (1-1).

The form of the modified gum arabic of the present invention is not particularly restricted, and it can take any form including blocks, beads, coarse pulverizates, granules, pellets, and powders (including spray dried powder).

As described above, the modified gum arabic of the present invention can be prepared by heating unmodified gum arabic (*A. senegal*) using a thermostat or heater such as an oven, for example, at 110° C. for not less than 10 hours. As examples of the unmodified gum arabic (*A. senegal*) as a raw material to be processed, the aforementioned ones may be used, and as specific heating methods, the above-described methods can be employed as well.

(1-3) The present invention provides water-soluble modified gum arabic that has a weight average molecular weight of not less than $9.0 \times 10^5$ (0.9 million) and AGP at the ratio of not less than 10 weight % that is obtained by heating unmodified gum arabic from *Acacia senegal*.

The weight average molecular weight is preferably at least $10.0 \times 10^5$ (1.0 million), more preferably at least $12.0 \times 10^5$ (1.2 million), still more preferably at least $15.0 \times 10^5$ (1.5 million), and yet more preferably at least $20.0 \times 10^5$ (2.0 million). Its upper limit is not particularly restricted as long as the modified gum arabic is soluble in water but is preferably approximately $25.0 \times 10^5$ (2.5 million) or less.

The content of AGP in the modified gum arabic is preferably not less than 15 weight %, more preferably not less than 17 weight %, and still more preferably not less than 20 weight %. Its upper limit is not particularly limited as long as the modified gum arabic is soluble in water but is preferably approximately 30 weight % or less.

The modified gum arabic provided by the present invention is characterized in that it has the above-mentioned properties and is soluble in water. Furthermore, it is preferable that the modified gum arabic of the present invention has the aforementioned weight average molecular weight and AGP content, be water-soluble, and has properties the same as or similar to unmodified gum arabic in terms of immunological reactivity. "Water-soluble" and "properties the same as or similar to unmodified gum arabic in terms of immunological reactivity" described here have the same meanings as stated in (1-1).

The form of modified gum arabic of the present invention is not particularly limited, and it can take any form including blocks, beads, coarse pulverizates, granules, pellets, and powders (including spray dried powder).

As described above, the modified gum arabic of the present invention can be prepared by heating unmodified gum arabic (*A. senegal*) using a thermostat or a heater such as an oven, for example at 110° C. for not less than 10 hours. As examples of the unmodified gum arabic (*A. senegal*) to be processed, the aforementioned ones may be used, and as specific heating methods, the above-described methods can be employed as well.

(2) Modified Gum Arabic Derived from *Acacia seyal*

(2-1) The present invention provides water-soluble modified gum arabic having a weight average molecular weight of not less than $25.0 \times 10^5$ (2.5 million) that is obtained by heating unmodified gum arabic from *Acacia seyal*.

In the present invention, the weight average molecular weight of the modified gum is not particularly restricted as long as it falls in the range described above, and is preferably not less than $26.0 \times 10^5$ (2.6 million), and even more preferably not less than $30.0 \times 10^5$ (3.0 million). The upper limit of the weight average molecular weight thereof is not restricted as long as the modified gum arabic is soluble in water but is preferably about $40.0 \times 10^5$ (4.0 million).

The modified gum arabic obtained by the present invention is characterized in that it has the above-mentioned weight average molecular weight and is soluble in water. Furthermore, it is preferable that modified gum arabic of the present invention has the above-mentioned weight average molecular weight, be water-soluble, and has properties the same as or similar to those of unmodified gum arabic in terms of immunological reactivity. "Water-soluble" and "properties the same as or similar to those of unmodified gum arabic in terms of immunological reactivity" described here have the same meanings as stated in (1-1).

The form of modified gum arabic of the present invention is not particularly limited, and it can take any form including blocks, beads, coarse pulverizates, granules, pellets, and powders (including spray dried powder).

The modified gum arabic of the present invention can be prepared by heating unmodified gum arabic (*A. seyal*) using a thermostat or a heater such as an oven, for example at 110° C. for not less than 10 hours.

The unmodified gum arabic (*A. seyal*) used as a raw material in this embodiment is a natural exudate from the trunks and branches of *Acacia seyal* of the genus *Acacia*, family Leguminasae or any other plant belonging to the same genus. It is also possible to use unmodified gum arabic that has been subjected to a treatment, such as purification treatment, desalting treatment, pulverization, or spray drying, etc.

The unmodified gum arabic (*A. seyal*) is generally produced in countries of North and West Africa from Ethiopia to Senegal (Ethiopia, Sudan, Senegal, Nigeria, Niger, and Ghana), countries of East Africa such as Kenya and Uganda, the Sahara region of Africa and the basins of tributaries of the Nile. The unmodified gum arabic (*A. seyal*) produced in any of the above areas can be employed as a raw material to be modified in the present invention regardless of its origin.

Furthermore, unmodified gum arabic (*A. seyal*) is not particularly restricted in its water content. Any commercially available unmodified gum arabic (*A. seyal*) can be used regardless of its water content.

The unmodified gum arabic (*A. seyal*) can usually be procured in such forms as blocks, beads, coarse pulverizates, granules, pellets, and powders (including spray dried powder). The unmodified gum arabic (*A. seyal*) of any form can be used without limitation as a raw material to be subjected the heat treatment of the present invention. It is possible to use spray dried gum arabic having an average particle diameter of several tens µm to several hundred µm. There is no particular upper limit to the average particle diameter but from the point of view of modification efficiency, the average particle diameter is preferably not more than 100 mm. The average particle diameter is preferably in the range from 1 mm to 100 mm and more preferably in the range from 2 mm to 50 mm.

Examples of the methods for heating unmodified gum arabic (*A. seyal*) include heating the unmodified gum arabic at 110° C. for not less than 10 hours using a thermostat or a heater as mentioned above. The preferable heat treatment is such that unmodified gum arabic (*A. seyal*) is heated at 110° C. for not less than 15 hours, more preferably for not less than 24 hours, and still more preferably for not less than 48 hours. While depending on the type of the unmodified gum arabic (*A. seyal*) to be subjected to heat treatment, the upper limit to the duration of heating when heated at 110° C. may be, for example, about 72 hours. As long as it is possible to obtain modified gum arabic that has the specific molecular weight defined in the present invention and that is soluble in water, the heating method is not limited to the above examples and heating temperature, duration of heating, heating means, and heating conditions (relative humidity, opened or closed system) can be optionally selected. The effects of the present invention achieved by the heat treatment conducted under the conditions described above can also be obtained by a method wherein the unmodified gum arabic is heated at a temperature lower than 110° C. for more than 10 hours or at a temperature higher than 110° C. for a shorter time. Specifically, the method for heating the unmodified gum arabic at 80° C. for 3 days to 1 week or longer may be mentioned as one example of the former case. When the unmodified gum arabic is heated using microwave radiation instead of an oven, the same effects can be achieved in less time. In addition, a heat treatment in the absence of oxygen, such as under nitrogen displacement conditions, is desirable because it can prevent discoloration of the gum arabic.

(2-2) The present invention also provides water-soluble modified gum arabic that contains more than 25 weight % of the protein-containing high molecular weight component that is obtained by heating gum arabic from *Acacia seyal*.

Figure 2:
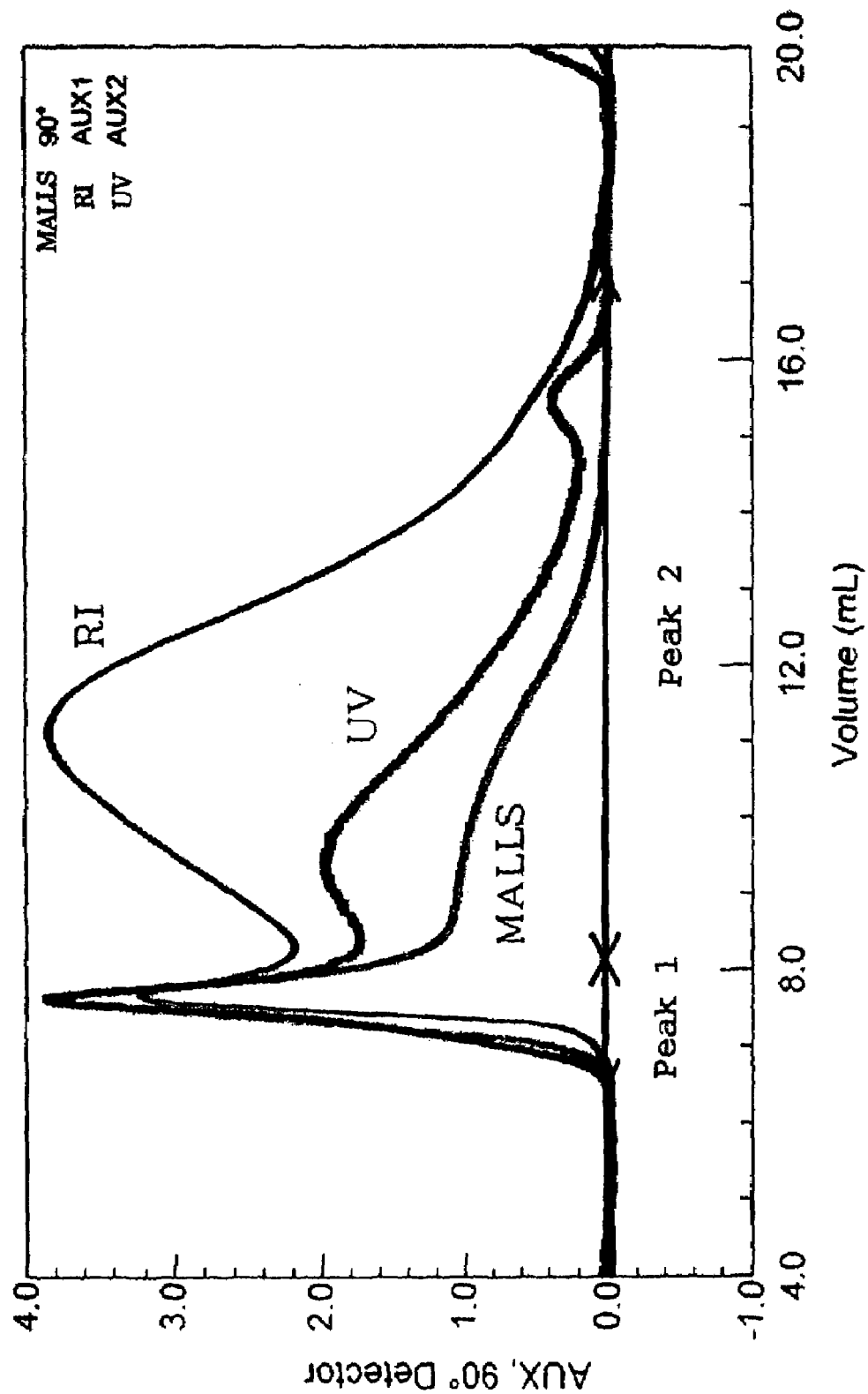
FIG. 2 shows chromatograms of gum arabic sample (untreated: natural gum arabic) from the *A. seyal* species obtained when it was subjected to GPC-MALLS mentioned in Experimental Example 1.

The content of the protein-containing high molecular weight component in the unmodified gum arabic from *Acacia seyal* and the modified gum arabic thereof can be determined by the GPC-MALLS mentioned above. Specifically, when RI chart of a chromatogram obtained using an RI detector is divided into two parts, i.e., Peak 1 (high molecular weight fraction) which traces the first eluted portion, and Peak 2 (low molecular weight fraction) which traces the later eluted portion, and the data are then processed with ASTRA Version 4.5 (Wyatt Technology) software, the recovery ratio of Peak 1 (% Mass) corresponds to the content (weight %) of the protein-containing high molecular weight component in the gum arabic. This is explained in detail with reference to the chromatogram (FIG. 2) showing the results wherein unmodified gum arabic (*A. seyal*) is analyzed using the GPC-MALLS. In the RI chromatogram, the point where the RI chart begins to rise from the baseline of the chromatogram is defined as the "starting point" and the point where the RI chart falls and intercepts the baseline is defined as the "ending point". Between the starting point and the ending point, the point where the RI value shows a minimum is defined as the boundary, with the area between the starting point and the boundary being defined as the Peak 1 and the area between the boundary and the ending point being defined as the Peak 2.

As with the *Acacia senegal*, the protein-containing high molecular weight component (peak 1) is one of the major components contained in the unmodified gum arabic (*A. seyal*). The unmodified gum arabic (*A. seyal*) generally contains this component at a ratio from 10 to 24 weight %.

The content of the protein-containing high molecular weight component (peak 1) in the modified gum arabic (*A. seyal*) of the present invention is not particularly limited as long as it falls within the above-mentioned range. However, it is preferably not less than 26 weight % and more preferably not less than 30 weight %. Its upper limit is not particularly restricted as long as the modified gum arabic is soluble in water; however, it is preferable that the content of the protein-containing high molecular weight component be about 45 weight % or less.

The modified gum arabic (*A. seyal*) obtained in the present invention is characterized in that it has the protein-containing high molecular weight component content in the above-mentioned range and is soluble in water. Furthermore, it is preferable that the modified gum arabic of the present invention contains the protein-containing high molecular weight component in the ratio mentioned above, be water-soluble, and has the properties the same as or similar to those of unmodified gum arabic (*A. seyal*) in terms of immunological reactivity. "Water-soluble" and "properties the same as or similar to those of unmodified gum arabic (*A. seyal*) in terms of immunological reactivity" described here have the same meanings as stated in (1-1).

There is no limitation to the form of modified gum arabic (*A. seyal*) of the present invention, and it can take any form including blocks, beads, coarse pulverizates, granules, pellets, and powders (including spray dried powder).

As described above, the modified gum arabic of the present invention can be prepared by heating unmodified gum arabic (*A. seyal*) using a thermostat or a heater such as an oven, for example at 110° C. for more than 10 hours. As examples of the unmodified gum arabic (*A. seyal*) to be modified, the aforementioned ones may be used, and as specific heating methods, the above-described methods can be employed as well (see (2-1)).

(2-3) The present invention also provides water-soluble modified gum arabic that has a weight average molecular weight of $15.0 \times 10^5$ (1.5 million) or greater and a content of the protein-containing high molecular weight component of not less than 22 weight % that is obtained by heating unmodified gum arabic from *Acacia seyal*.

The weight average molecular weight of the water-soluble modified gum arabic (*A. seyal*) is preferably at least $20.0 \times 10^5$ (2.0 million) and more preferably at least $25.0 \times 10^5$ (2.5 million). There is no particular upper limit thereof as long as the modified gum arabic (*A. seyal*) is water-soluble but generally it is, for example, about $40.0 \times 10^5$ (4.0 million) or less.

The content of the protein-containing high molecular weight component (peak 1) in the modified gum arabic (*A. seyal*) is preferably not less than 25 weight % and more preferably not less than 30 weight %. There is no particular upper limit thereof as long as the modified gum arabic is water-soluble but generally it is, for example, about 45 weight % or less.

The modified gum arabic (*A. seyal*) obtained by the present invention is characterized in that it has the above-mentioned properties and is soluble in water. Furthermore, it is preferable that the modified gum arabic of the present invention has the above-described weight average molecular weight and content of the protein-containing high molecular weight component, be water-soluble, and has properties the same as or similar to unmodified gum arabic in terms of immunological reactivity. "Water-soluble" and "properties the same as or similar to unmodified gum arabic (*A. seyal*) in terms of immunological reactivity" as described here have the same meanings as stated in (1-1).

The form of the modified gum arabic (*A. seyal*) of the present invention is not particularly restricted, and it can take any form including blocks, beads, coarse pulverizates, granules, pellets, and powders (including spray dried powder).

As described above, the modified gum arabic of the present invention can be prepared by heating unmodified gum arabic (*A. seyal*) using a thermostat or a heater, such as an oven, for example at 110° C. for not less than 10 hours. As examples of unmodified gum arabic (*A. seyal*) to be modified, the aforementioned ones may be used, and as specific heating methods, the above-described methods can be employed as well (see (2-1)).

The modified gum arabic of the present invention, especially the modified gum arabic derived from the species *A. senegal* provided at any one of the above (1-1) to (1-3), can be clearly distinguished from the unmodified gum arabic in terms of emulsifiability. The modified gum arabic, especially the modified gum arabic derived from the species *A. senegal*, has higher emulsifiability than the unmodified gum arabic.

The modified gum arabic of the present invention, especially the modified gum arabic derived from the species *A. seyal* provided at any one of the above (2-1) to (2-3), can also be clearly distinguished from the unmodified gum arabic in terms of emulsifiability, emulsion stability, encapsulation ability, adhesiveness, protective colloid property or filmforming ability. The modified gum has an improved emulsifiability, emulsion stability, encapsulation ability, adhesiveness, protective colloid property or filmforming ability relative to that of the unmodified gum arabic.

The emulsifiability of the modified gum arabic, especially the modified gum arabic derived from the species *A. senegal*, can be evaluated by measuring the average particle diameter of droplets in an emulsion (dispersed phase), when the emulsion is prepared using it. It is preferable that the average particle diameter of droplets in the emulsion prepared using the modified gum arabic is generally not greater than 1 μm, preferably not greater than 0.8 μm, more preferably not greater than 0.7 μm, and still more preferably not greater than 0.6 μm. The emulsion for use in this evaluation can be prepared according to a method described in Experimental Example 1 (2).

Furthermore, it is preferable that the obtained emulsion be stable over time. This emulsion stability over time can be evaluated by measuring the average particle diameter of emulsion immediately after preparation [average particle diameter (a)] and the average particle diameter of emulsion at several days (2-7 days) after storing at 60° C. [average particle diameter (b)], respectively, and obtaining the difference between the two values [(b)−(a)]. Although it is not restricted, in the case of an emulsion has been stored for 7 days at 60° C., it is preferable that such difference be 1 μm or less, more preferably 0.3 μm or less, and still more preferably 0.1 μm or less.

(3) The modified gum arabic according to the invention, especially the modified gum arabic derived from the species *A. senegal*, is suitable as an emulsifier for preparing varied emulsions, especially oil-in-water (O/W) or W/O/W emulsions in foods, pharmaceuticals, Medicine, quasi-drugs, perfume, cosmetics and other fields. The modified gum arabic is extremely suitable as an emulsifier for preparing products which are taken orally, such as foods, pharmaceuticals, and quasi-drugs. The present invention provides an emulsifier comprising the above-mentioned modified gum arabic as an active component.

To be more specific, the modified gum arabic of the present invention can be suitably used as an emulsifier to emulsify; foods or constituents thereof, such as confectionery (for example, candy, chewing gums, cough drops, candy lozenges, gum drops, jujubes, pastille, tablet confections, dry snacks, etc.,), dairy products or frozen products (for example, ice cream, ice and sherbets, package-able milk and cream, etc.,), bakery products, beverages (for example, drinks, powdered drinks), desserts, processed fish products, processed stock farm products, retort foods, etc.; coatings for foods or pharmaceuticals such as a tablet, etc.; oil-based flavorings or cosmetics; or oil-based colorants, etc.

The above-described modified gum arabic per se can be used without additives as an emulsifier when formed into a solution, a granular, or powder; however, it is also possible to prepare it as an emulsifier by adding other carriers and/or additives according to the usual manner in the above-mentioned fields, if necessary. In this case, the carriers and additives can be suitably selected according to the usual manner using natural gum arabic as an emulsifier in the above-mentioned fields, depending on the type and usage of the product to be emulsified. For example, modified gum arabic can be added with dextrin, maltose, lactose and like saccharide, or glycerol, propylene glycol and like polyhydric alcohols. In this embodiment, Document 1 (Roy L. Whistlerand James N. BeMiller, "INDUSTRIAL GUMS—Polysaccharides and Their Derivatives", SECOND EDITION, ACADEMIC PRESS, New York and London, 1973, pp,197-263) and Document 2 (Martin Glicksman, "Gum Technology in the Food Industry" ACADEMIC PRESS, New York and London, 1969, pp,94-124) can be used as reference.

(4) The present invention further provides a method for preparing an emulsion using the above-mentioned modified gum arabic as an emulsifier, especially the above-mentioned modified gum arabic derived from *A. senegal*. This emulsion can be prepared by dispersing and stabilizing a hydrophobic substance, which is a dispersoid, in a hydrophilic solvent using the above-mentioned modified gum arabic as an emulsifier. Examples of emulsion shown in the present invention include an oil-in-water (OW) emulsion or a W/O/W emulsion.

The hydrophobic substance to be emulsified in this invention is not particularly restricted as long as it is a substance which can be generally formed into an emulsion or must be processed into an emulsion; however, hydrophobic substances which are used in the field of foods, pharmaceuticals, quasi-drugs or fragrances and cosmetics are preferable, and hydrophobic substances that can be taken orally, i.e., edible hydrophobic substances are especially preferable.

Specific examples include essential oils derived from plant sources, for example, citrus plants such as orange, lime, lemon, grapefruit, etc.; oleoresins derived from plant sources such as pepper, cinnamon, ginger, etc.; absolutes derived from plant sources such as jasmine, rose, etc.; oil-based flavorings such as oil-based synthetic flavorings and oil-based blending flavorings, etc.; oil-based colorants such as β-carotene, paprika color, lycopene, palm oil carotene, Donalliella carotene, carrot carotene, etc.; oil-soluble vitamins such as vitamin A, D, E, and K; polybasic unsaturated fatty acids such as $C_{18}$-$C_{22}$ polybasic unsaturated fatty acids including n–6 type polybasic unsaturated fatty acids (linoleic acid, γ-linolenic acid, and arachidonic acid, etc.) and n–3 type polybasic unsaturated fatty acids (α-linolenic acid, docosahexaenoic acid, and eicosapentanoic acid, etc.); animal and vegetable fats and oils such as soybean oil, rapeseed oil, corn oil and fish oil; SAIB (sucrose acetate isobutyrate), food processing oils such as $C_6$-$C_{12}$ medium-chain triglycerides, and optionally mixtures of such edible oil-based materials.

The method for preparing an emulsion using the above-described modified gum arabic is not particularly restricted and may comprise a step of mixing a hydrophobic substance and a hydrophilic solvent in the presence of the modified gum arabic according to standard method for preparing oil-in-water (O/W) emulsions or W/O/W emulsions, preferably by mechanical agitation, for example using a homogenizer or a high-pressure injection system. In particular, the following process can be mentioned as an example.

First, the modified gum arabic is dissolved in a hydrophilic solvent such as water, and, if necessary, contaminants are removed by a suitable solid-liquid separation means such as centrifugation or filtration with a filter press or the like, giving an aqueous gum arabic solution. An objective hydrophobic substance (for example, an oil or fat or a mixture obtained by dissolving a flavoring or a color in such an oil or fat) is admixed with the obtained aqueous gum arabic solution using a stirrer for preliminary emulsification. During this process, its specific gravity may be adjusted using a specific gravity control agent such as SAIB. The preliminary emulsion thus obtained is then emulsified using emulsifying equipment.

Examples of usable hydrophobic substances include the substances mentioned above. However, when an emulsified flavoring or an emulsified color is to be prepared using oil-based flavoring or color, it is preferable to use a solution mixture wherein an oil-based flavoring or color is dissolved beforehand in oil or fat as the hydrophobic substance. This makes it possible to stabilize the emulsion and prevent the evaporation of components. The oils and fats in which such an oil-based flavoring or color is to be dissolved are not particularly restricted but usually medium-chain triglycerides ($C_{6-12}$ fatty acid triglycerides) and vegetable oils such as corn oil, safflower oil and soybean oil can be employed.

There is no limitation to the emulsifying equipment used and it can be suitably selected according to the droplet size of the objective emulsion and the viscosity of the material. For example, a homogenizer, a pressurized homogenizer and other emulsifying equipment, such as a Disper Mill, a colloid mill, etc., can be employed.

The emulsification can be conducted by adding a hydrophobic substance to a hydrophilic solvent while stirring, performing preliminary emulsification to prepare an emulsion having a particle diameter of 2-5 μm, and treating it with an emulsifying equipment such as a homogenizer to give an emulsion having fine and uniform particles (for example, average particle diameter of not greater than 1 μm).

Many colorants including β-carotene exist in the form of crystal suspensions. Therefore, to process such colorants into emulsions (emulsified colorants), it is preferable to mix and dissolve crystals of color in a suitable oil or fat at an elevated temperature beforehand, and then add the resulting solution into a hydrophilic solvent.

Compared with an emulsion prepared using natural (unmodified) gum arabic, an emulsion prepared using the modified gum arabic of the invention has a uniform particle diameter and is very stable, so that emulsified particles are significantly prevented from coagulation or unification of the emulsified particles caused by hard dealing or under severe conditions such as heating, long-term storage, etc.

(5) The modified gum arabic of the present invention especially that derived from the species *A. seyal*, can be suitably used as a thickener, binder, coating agents, suspending agents, sizing and finishing agents, material for capsules (encapsulant) and the other, in the foods, pharmaceuticals, quasi-drugs, flavor/cosmetic, inks, paints, adhesives, lithography, texiles industries due to its improved and enhanced emulsifiability, emulsion stability, encapsulation ability, adhesiveness, protective colloid property and filmforming ability. Therefore, the present invention provides a thickener, binder, coating agent and material for capsules (encapsulant) wherein the aforementioned modified gum arabic, especially the modified gum (*A. seyal*), serves as an active component. The thickener, binder, coating agent or material for capsules (encapsulant) is prepared according to the usual manner in the field, except for using the modified gum arabic of the present invention as an active component.

In this embodiment, Document 1 (Roy L. Whistlerand James N. BeMiller, "INDUSTRIAL GUMS—Polysaccharides and Their Derivatives", SECOND EDITION, ACADEMIC PRESS, New York and London, 1973, pp,197-263) and Document 2 (Martin Glicksman, "Gum Technology in the Food Industry" ACADEMIC PRESS, New York and London, 1969, pp,94-124) can be used as reference.

EXAMPLES

The present invention will be described below in detail with reference to the following Experimental Examples and Examples, but is not limited to these Examples. In each Example, unless otherwise specified, "part" means "part by weight" and "%" means "% by weight". In each formulation, a substance marked by "*" means the product of San-Ei Gen F.F.I. Inc.

Experimental Example 1

Modification of Gum Arabic and Evaluation of the Obtained Modified Gum Arabic 70 kg of cracked gum arabic (*A. senegal:* Sample 1) (5 mm particle size) was charged into a 100 L volume stainless steel drum and was then heated at 110° C. for 36 hours to give 'sample 1/36'. These gum arabic samples (Sample 1 and Sample 1/36) were subjected to GPC-MALLS under the following conditions to obtain chromatographs.

<Conditions of GPC-MALLS>
  Column: Superose (6HR) 10/30 (Pharmacia Biotech)
  Flow rate: 0.5 ml/min.
  Elution solvent: 0.2 M NaCl
  Preparation of a sample: the assay samples were dissolved with the elution solvent (0.2 M NaCl)
  Sample concentration: 0.4% (W/V)
  Sample charge volume: 100 µl
  dn/dc: 0.141
  Temperature: room temperature
  Detector: (1) MALLS (multi angle laser light scattering) detector: DAWN DSP (Wyatt Technology),
    (2) RI (refractive index) detector,
    (3) UV detector (absorption at 214 nm)

The chromatograms obtained from the Sample 1 and Sample 1/36 are shown in FIGS. 1(A) and (B), respectively. "Volume (ml)" corresponding to the abscissa shows the cumulative volume of the elution solvent passing through the column and 'AUX, 90° Detector' corresponding to the ordinate shows the relative intensity of each detector (MALLS detector, RI detector, and UV detector). The chromatogram (MALLS chart) obtained by the MALLS detector indicates the light scattering intensity at 90°, which correlates with the molecular weight distribution. The RI chromatogram (RI chart) obtained with the RI detector indicates the refractive index intensity, which correlates with the weight of component containing in each eluate. The UV chromatogram (UV chart) shows the UV absorption at 214 nm, which correlates with the protein distribution.

Based on the RI chart obtained with the RI detector, the eluted components can be classified into two fractions; an eluted fraction of high molecular weight components which eluted first (Peak 1 area shown in FIG. 1), and an eluted fraction of low molecular weight components which eluted at a later time (Peak 2 area shown in FIG. 1). More specifically, the point at which the RI chart (RI curve) begins to rise from the baseline of the chromatogram is defined as the 'starting point', and the point at which the RI chart (RI curve) falls and intersects the baseline is defined as the 'ending point'. The point at which the RI intensity shows a minimum between the starting point and the ending point is defined as a boundary. The peak area between the starting point and the boundary is the aforesaid eluted fraction of high molecular weight components (Peak 1 area), and the peak area between the boundary and the ending point is the aforesaid eluted fraction of low molecular weight components (Peak 2 area).

The eluted fraction of high molecular weight components (Peak 1 area) is the fraction containing the highest protein content and the recovery ratio (% mass) thereof is corresponding to the arabinogalactan protein (AGP) content of the gum arabic. Comparison between FIG. 1 (A) showing the elution profiles of gum arabic (*A. senegal*) (Sample 1) and FIG. 1(B) showing the elution profiles of the heated gum arabic (*A. senegal*) (sample 1/36) shows the following.

The eluted fraction of the highest molecular weight protein component (AGP) (Peak 1 area) in Sample 1 (unmodified gum arabic) exhibited a low measured value with the light scattering detector (MALLS detector) monitored at 90° (peak height: about 1.3), low RI measured value (small amount) and a broadened UV absorption. In contrast, the eluted fraction of the highest molecular weight protein component (AGP) (Peak 1 area) in Sample 1/36 (heated gum arabic) shows a high measured value with the MALLS detector (peak height: about 8), a high RI intensity (large amount) and a sharp UV absorbance peak.

A weight average molecular weight, recovery ratio (% mass), polydispersity value (P), and root mean square (RMS) radius of gyration (Rg) were obtained by processing the data obtained under the above-described conditions using ASTRA Version 4.5 (Wyatt Technology) software.

Weight average molecular weight ($M_{wt}$) (in more detail, $M_{wt}$ processed as one peak) used in the present invention is defined as the molecular weight obtained when the whole peaks in the chromatogram obtained with the RI detector was data-processed as one peak. The said whole peaks mean one presented in the area from a starting point to an ending point, when the point at which the RI chart (RI curve) begins to rise from the baseline of RI chromatogram is defined as the 'starting point', and the point at which the RI chart (RI curve) falls and intersects the baseline is defined as the 'ending point'. Recovery ratio (% mass) of the Peak 1 area shows the AGP content of gum arabic (natural gum arabic (*A. senegal*), modified gum arabic (*A. senegal*)). RMS-radius of gyration (Rg) is used as an indicator of molecular size. The Rg value corresponds to the molecular weight, and thus an increased molecular weight corresponds to an increased Rg value. Polydispersity (P) value is defined as the ratio of weight average molecular weight ($M_w$) to the number average molecular weight ($M_n$) [i.e ($M_w/M_n$)]. When P value is high, peaks in the RI chromatogram become broad, which indicates that the molecular weight has highly variable (polydispersity) (peaks of various molecular weight exist intermixed). When P value is low, peaks in the RI chromatogram become sharp, which indicates that the polydispersity is low.

These parameters were determined by two kinds of data-processing: by data-processing as one peak the whole peaks in the chromatogram obtained with the RI detector, and by data-processing as two peaks with the chart divided into the eluted fraction of high molecular weight components which eluted first (Peak 1 area) and the eluted fraction of low molecular weight components which eluted a later time (Peak 2 area) as shown in FIGS. 1(A) and (B). The results are shown in Table 1.

TABLE 1

| | Parameters processed as one peak | | | | Parameters processed as two peaks | | | |
|---|---|---|---|---|---|---|---|---|
| Sample | $M_{wt}$[1] | % Mass | P | Rg | $M_{wt}$ | % Mass | P | Rg |
| 1 | $5.36 \pm 0.02 \times 10^5$ | 101 | 2.01 | 20.4 | $2.30 \pm 0.01 \times 10^6$ | 8.1[2] | 1.19 | 34.0 |
| | | | | | $3.74 \pm 0.01 \times 10^5$ | 92.9 | 1.56 | 18.9 |
| 1/36 | $1.97 \pm 0.04 \times 10^6$ | 101 | 4.62 | 33.6 | $9.44 \pm 0.25 \times 10^6$ | 16.1[2] | 1.79 | 54.5 |
| | | | | | $5.16 \pm 0.03 \times 10^5$ | 84.9 | 1.44 | 27.7 |

[1]Weight average molecular weight of the gum arabic sample
[2]Arabinogalactan protein content of the gum arabic sample (% by weight)

These results show that, by heat treatment the gum arabic, the weight average molecular weight thereof increased from about $5.36 \times 10^5$ (Sample 1) to about $1.97 \times 10^6$ (Sample 1/36) and the AGP thereof was increased from about 8.1% (Sample 1) to 16.1% (Sample 1/36).

(2) Evaluation of Emulsifying Ability

Emulsions were prepared using the above gum arabic samples (Sample 1 and Sample 1/36) according to the method given below, and emulsifiability of each sample was evaluated by determining the average particle diameter and the storage stability of the emulsions.

More specifically, the obtained samples (Sample 1 and Sample 1/36) were each dissolved in water, centrifuged to remove insolubles and prepared into 7.5%, 10%, 15% and 20% aqueous solutions of gum arabic. To 800 g of each of these aqueous solutions was added 200 g of medium-chain triglyceride (octanoic/decanoic acid triglyceride O.D.O. (trade name, product of Nisshin Oil Mills, Ltd.)) while stirring, and the mixtures were emulsified using a homogenizer (manufactured by APV Gaulin) (homogenized 4 times at a pressure of 44 MPa (450 kg/cm$^2$)), giving emulsions. The average particle diameter of the resulting emulsions was measured immediately after emulsification and after 2 days of storage at 60° C. using a particle size distribution analyzer (SALD-1100 Laser Diffraction Particle Size Analyzer, manufactured by Shimadzu).

Generally, the emulsifiability of an emulsifier is superior as the average particle diameter of the emulsion prepared using the emulsifier is smaller and the particle diameter is held more stably over time ("the Study by the turbidimetric assay method of O/W emulsion emulsified with gum arabic", Yakugaku Zasshi (Pharmacology Journal), 112(12)906-913, (1992)).

The average particle diameter and the storage stability of the emulsions prepared using each gum arabic sample (Sample 1 and Sample 1/36) are shown in Table 2. The storage stability can be determined based on the difference [(b)–(a)] between the average particle diameter of the emulsions immediately after emulsification (a) and the average particle diameter of the emulsions after an accelerated test (2 days of storage at 60° C.) (b).

TABLE 2

| | Average particle diameter of emulsions (μm) | | | | | |
|---|---|---|---|---|---|---|
| | Sample 1 | | | Sample 1/36 | | |
| Aqueous solution of gum arabic | Immediately after emulsification | After accelerated test (2 days storage at 60° C. | Change | Immediately after emulsification | After accelerated test (2 days storage at 60° C. | Change |
| 7.5 | 0.98 | 3.73 | 2.75 | 0.82 | 0.83 | 0.01 |
| 10 | 0.88 | 2.95 | 2.07 | 0.72 | 0.73 | 0.01 |
| 15 | 0.74 | 2.10 | 1.36 | 0.65 | 0.66 | 0.01 |
| 20 | 0.68 | 1.54 | 0.86 | 0.63 | 0.64 | 0.01 |

The smaller is the change in the average emulsion particle diameter, the better is the storage stability of the emulsion. Conclusions can be drawn considering the average emulsion particle diameter as follows:

'Excellent emulsifiability': when the change in the average emulsion particle diameter is less than 0.1 μm;

'Moderately good emulsifiability': when the change in the average emulsion particle diameter ranges from 0.1 μm to 1 μm; and 'Bad emulsifiability': when the change in the average emulsion particle diameter is 1 μm or more.

As can be seen from Table 2, in terms of emulsifiability, the unmodified gum arabic (Sample 1) was bad, whereas the heated gum arabic (Sample 1/36) was superior since the average particle diameter change was less than 0.1 μm.

Experimental Example 2

Modification of Gum Arabic and Evaluation of the Obtained Modified Gum Arabic 1 kg of cracked gum arabic belonging to *Acasia Senegal* species (natural gum arabic from *A. senegal:* 'Sample 2') (5 mm particle size) was placed in an unsealed stainless steel container, exposed to the air and heated at 110° C. for 24 hours and 48 hours using an oven (gum arabic samples heated for 24 hours and 48 hours are referred to as 'Sample 2/24' and 'Sample 2/48', respectively). These gum arabic samples (Sample 2, Sample 2/24 and Sample 2/48) were subjected to GPC-MALLS and the chromatogram was obtained in the same manner as in Experimental Example 1. A weight average molecular weight, recovery ratio (% mass), polydispersity (P) value and RMS-radius of gyration (Rg) were obtained by processing the obtained data using ASTRA Version 4.5 (Wyatt Technology) software. These parameters were determined by two kinds of data-processing: by data-processing as one peak the whole peaks in the chromatogram obtained with the RI detector, and by data-processing as two peaks with the chart divided into an eluted fraction of high molecular weight components which eluted first (Peak 1 area) and an eluted fraction of low molecular weight components which eluted a later time (Peak 2 area). The results are shown in Table 3.

The results showed that, by heat treatment the gum arabic, the weight average molecular weight thereof was increased from about $4.13 \times 10^5$ (Sample 2) to about $8.62 \times 10^5$ (Sample 2/24) or about $1.43 \times 10^6$ (Sample 2/48) and the AGP content thereof was increased from about 7.38% (Sample 2) to 17.3% (Sample 2/24) or 20.2% (Sample 2/48).

(2) Evaluation of Emulsifying Ability

Emulsions were prepared using the above gum arabic samples (Sample 2, Sample 2/24 and Sample 2/48), according to the method given below, and the average particle diameter and the storage stability of the emulsions were determined to evaluate emulsifiability of each sample.

More specifically, 1 kg of each of the obtained samples (Sample 2, Sample 2/24 and Sample 2/48) was dissolved in 4 kg of water, centrifuged to remove insolubles, and prepared into 20% aqueous solution of each gum arabic sample. To 850 g of 20% aqueous solution of each sample was added 150 g of medium-chain triglyceride (octanoic/decanoic acid triglyceride O.D.O. (trade name, product of Nisshin Oil Mills. Ltd.) while stirring, and each mixture was emulsified using a homogenizer (manufactured by APV Gaulin) (homogenized 4 times at a pressure of 44 MPa (450 kg/cm$^2$)), giving emulsions. The average particle diameter of the obtained emulsions was measured immediately after emulsification and

TABLE 3

| | Parameters processed as one peak | | | | Parameters processed as two peaks | | | |
|---|---|---|---|---|---|---|---|---|
| Sample | $M_{wt}$[1] | % Mass | P | Rg | $M_{wt}$ | % Mass | P | Rg |
| 2 | $4.13 \pm 0.15 \times 10^5$ | 106 | 2.14 | 28.1 | $1.87 \pm 0.19 \times 10^6$ | 7.38[2] | 1.23 | 34.4 |
| | | | | | $3.04 \pm 0.11 \times 10^5$ | 98 | 1.67 | 24.7 |
| 2/24 | $8.62 \pm 0.36 \times 10^5$ | 116 | 2.99 | 36.4 | $3.52 \pm 0.14 \times 10^6$ | 17.3[2] | 1.56 | 42.3 |
| | | | | | $3.97 \pm 0.16 \times 10^5$ | 97 | 1.58 | 24.7 |
| 2/48 | $1.43 \pm 0.06 \times 10^6$ | 102 | 3.68 | 42.5 | $5.29 \pm 0.23 \times 10^6$ | 20.2[2] | 1.76 | 46.3 |
| | | | | | $4.79 \pm 0.18 \times 10^5$ | 82 | 1.49 | 29.6 |

[1]Weight average molecular weight of the gum arabic sample
[2]Arabinogalactan protein content of the gum arabic sample (% by weight)

Figure 3:
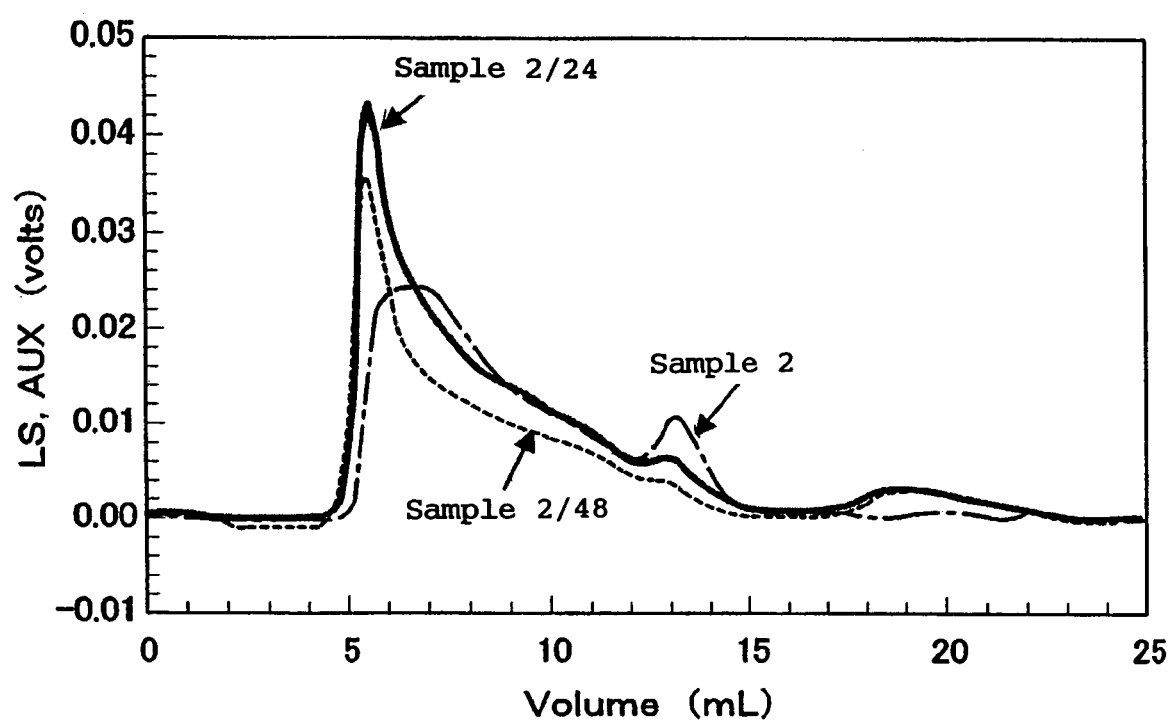
FIG. 3 shows the UV absorption profile (wavelength: 214 nm) of Samples 2, 2/24 and 2/48 prepared in Experimental Example 2 obtained on the basis of GPC-MALLS, which indicate the protein distribution thereof.
Figure 4:
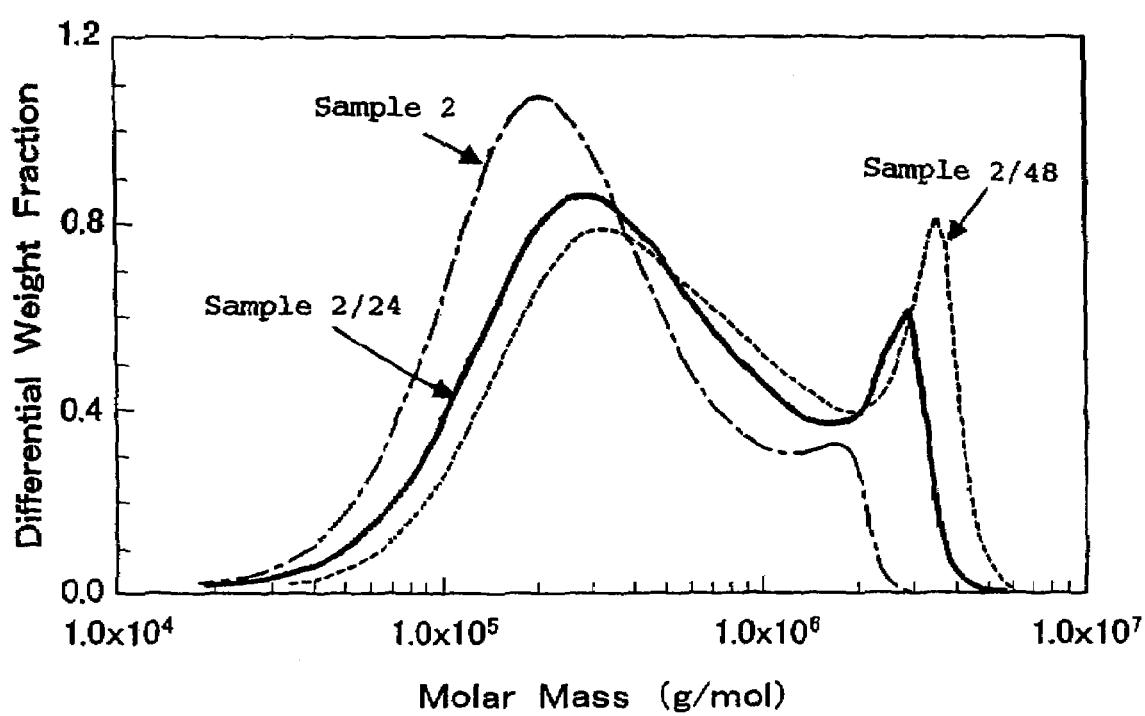
FIG. 4 shows the molecular weight distribution of Samples 2, 2/24 and 2/48 prepared in Experimental Example 2, which is obtained on the basis of GPC-MALLS.

A UV absorption profile (wavelength: 214 nm) indicating the protein distribution of each sample is shown in FIG. 3 and a profile indicating the molecular weight distribution of each sample is shown in FIG. 4. In FIG. 3, the X axis plots the cumulative amount of eluate from the column (mL) (Volume (mL)) and the Y axis plots the relative intensity of the UV response at a wavelength of 214 nm (LS, AUX (volts)).

The molecular weight of each of the gum arabic samples (Sample 2, Sample 2/24 and Sample 2/48) at the maximum point of the RI curve (Mp/RI$_{max}$) and the maximum point of the UV curve (Mp/UV$_{max}$) is shown in Table 4.

after 7 days of storage at 60° C. using a particle size distribution analyzer (SALD-1100 Laser Diffraction Particle Size Analyzer, manufactured by Shimadzu).

The average particle diameter and the storage stability of the emulsions prepared using each gum arabic sample (Sample 2, Sample 2/24 and Sample 2/48) are shown in Table 5. The storage stability was determined based on the difference [(b)−(a)] between the average particle diameter immediately after emulsification (a) and the average particle diameter of the emulsion after an accelerated test (7 days of storage at 60° C.) (b).

TABLE 4

| Sample | Mp/RI$_{max}$ | Vol. (ml) | Rg | Mp/UV$_{max}$ | Vol. (ml) | Rg |
|---|---|---|---|---|---|---|
| 2 | $1.74 \pm 0.06 \times 10^6$ | 6.008 | 33.4 | $1.06 \pm 0.03 \times 10^6$ | 6.667 | 29.9 |
| 2/24 | $3.01 \pm 0.06 \times 10^6$ | 5.842 | 37.9 | $4.38 \pm 0.01 \times 10^6$ | 5.608 | 40.4 |
| 2/48 | $3.97 \pm 0.12 \times 10^6$ | 5.817 | 40.9 | $9.86 \pm 0.33 \times 10^6$ | 5.517 | 44.5 |

TABLE 5

| Sample | Group of emulsifiability | Average particle diameter of emulsion immediately after emulsification (μm) [a] | Average particle diameter of emulsion after accelerated test (7 days at 60° C.) (μm) [b] | Particle diameter change (μm) ([b] − [a]) |
|---|---|---|---|---|
| 2 | C | 0.63 | 2.12 | 1.49 |
| 2/24 | A | 0.51 | 0.51 | 0 |
| 2/48 | A | 0.51 | 0.51 | 0 |

The above table shows that the smaller the change of the emulsion droplet size (average particle diameter), the better the storage stability. Emulsifying ability of each Sample was classified 3 groups based on the change of the average particle diameter (the emulsion droplet size.) as follows:

'Excellent emulsifiability (Group A)': when the change of the average particle diameter is less than 0.1 μm, 'Moderately good emulsifiability (Group B)': when the change of the average particle diameter ranges from 0.1 μm to 1 μm, and 'Bad emulsifiability (Group C)': when the change of the average particle diameter is 1 μm or more.

Consequently, as shown in Table 5, the unmodified gum arabic (Sample 2) is classified as Group C, showing bad emulsifying ability, whereas the heat-treated gum arabic samples of both Sample 2/24 and Sample 2/48 are classified as Group A, showing superior emulsifying abilities. There are relationships between properties and emulsifiability of gum arabic as listed in the followings (1) to (4), based on FIG. 3 shown the UV absorption profile, FIG. 4 shown the molecular weight profile and Tables 3 and 4 shown the various parameters, which are indicated by contrasting the heat-treated Samples 2/24 and 2/48 in Group A (superior emulsifying ability) with Sample 2 in Group C (bad emulsifying ability).

(1) As the weight average molecular weight increases, the emulsifiability improves. Specifically, the weight average molecular weight of the modified gum arabic should be preferably 0.9 million or more, more preferably 1.2 million or more, still more preferably 1.5 million or more, and further more preferably 2 million or more, in terms of emulsifiability.

(2) As the AGP content increases, the emulsifiability improves. Specifically, the AGP content should be preferably 12% or more, more preferably 17% or more, and still more preferably 20% or more, in terms of emulsifiability.

(3) As the molecular weight at the maximum point of the RI curve ($Mp/RI_{max}$) and the molecular weight at the maximum point of the UV curve ($Mp/UV_{max}$) become higher, the emulsifiability improves. In particular, the molecular weight is preferably 4,000,000 or more at the maximum point of the UV trace ($MP/w_{max}$), in terms of emulsifiability.

(4) As the shape of the first peak in the UV chart becomes sharper, the emulsifiability become better.

This process (heat-treatment) allows the re-distribution of proteins of the natural gum arabic (in other words, this process (heat-treatment) allows the protein distribution of gum arabic to be changed) to increase the AGP content which enhances the emulsifi ability.

Experimental Example 3

1 kg of cracked gum arabic (*A. senegal*: 'Sample 3') (5 mm particle size) was heated at 110° C. for 24 hours and 48 hours using an oven in the same manner as in Experimental Example 2. The gum arabic samples heated for 24 hours and 48 hours are referred to as 'Sample 3/24' and 'Sample 3/48', respectively. These gum arabic samples (Sample 3, Sample 3/24 and Sample 3/48) were subjected to GPC-MALLS and the chromatograms were obtained in the same manner as in Experimental Example 1. Various parameters (weight average molecular weight, recovery ratio (% mass), polydispersity (P) value, and RMS-radius of gyration (Rg)) were obtained by processing the obtained data in the same manner as in Experimental Example 1. The weight average molecular weight ($M_{wt}$ processed as one peak) of the gum arabic samples (Sample 3, Sample 3/24 and Sample 3/48) is shown in Table 6.

TABLE 6

| Sample | $M_{wt}$ processed as one peak[1] | % by mass | |
|---|---|---|---|
| 3 | $5.15 \pm 0.18 \times 10^5$ | 101 | Control |
| 3/24 | $1.15 \pm 0.21 \times 10^6$ | 105 | Heated at 110° C. for 24 hours |
| 3/48 | $1.91 \pm 0.17 \times 10^6$ | 103 | Heated at 110° C. for 48 hours |

[1]Weight average molecular weight of the gum arabic sample

Experimental Example 4

1 kg of spray-dried gum arabic (*A. senegal:* 'Sample 4') (powder form) was heated at 110° C. for 24 hours using an oven (gum arabic heated for 24 hours is referred to as 'Sample 4/24') in the same manner as in Experimental Example 2. These gum arabic samples (Sample 4 and Sample 4/24) were subjected to GPC-MALLS and chromatograms were obtained in the same manner as in Experimental Example 1. Various parameters (weight average molecular weight, recovery ratio (% mass), polydispersity (P) value, and RMS-radius of gyration (Rg)) were obtained by processing the obtained data in the same manner as in Experimental Example 1. The results are shown in Table 7.

TABLE 7

| Sample | Parameters processed as one peak | | | | Parameters processed as two peaks | | | |
|---|---|---|---|---|---|---|---|---|
| | $M_{wt}$[1] | % by Mass | P | Rg | $M_{wt}$ | % by Mass | P | Rg |
| 4 | $5.99 \pm 0.2 \times 10^5$ | 107 | 2.24 | 25 | $2.34 \pm 0.09 \times 10^6$ | 14.55[2] | 1.49 | 35.2 |
| | | | | | $3.19 \pm 0.08 \times 10^5$ | 93.1 | 1.34 | — |
| 4/24 | $1.43 \pm 0.26 \times 10^6$ | 102 | 4.66 | 97.6 | $6.38 \pm 0.91 \times 10^6$ | 18[2] | 2.78 | 109 |
| | | | | | $3.82 \pm 0.08 \times 10^5$ | 83.3 | 1.45 | 19 |

[1] Weight average molecular weight of the gum arabic sample
[2] Arabinogalactan protein content of the gum arabic sample (% by weight)

Experimental Example 5

1 kg of spherical cluster of gum arabic (*A. Senegal*: 'Sample 5') (cluster size of 20 mm×30 mm or less) was heated at 110° C. for 24 hours using an oven (gum arabic heated for 24 hours is referred to as 'Sample 5/24') in the same manner as in Experimental Example 2. These gum arabic samples (Sample 5 and Sample 5/24) were subjected to GPC-MALLS and chromatograms were obtained in the same manner as in Experimental Example 1. Various parameters (weight average molecular weight, recovery ratio (%. mass), polydispersity (P) value, and RMS-radius of gyration (Rg)) were obtained by processing the obtained data in the same manner as in Experimental Example 1. The results are shown in Table 8.

Experimental Example 6 cracked gum arabic (*A. seyal*: 'Sample 6') (5 mm particle size) was heated at 110° C. for 15 hours using an oven (gum arabic heated for 15 hours is referred to as 'Sample 6/15') in the same manner as in Experimental Example 2. These gum arabic samples (Sample 6 and Sample 6/15) were subjected to GPC-MALLS and chromatograms were obtained in the same manner as Experimental Example 1. Various parameters (weight average molecular weight, recovery ratio (% mass), polydispersity (P) value, and RMS-radius of gyration (Rg)) were obtained by processing the obtained data in the same manner as in Experimental Example 1. The results are shown in Table 9.

TABLE 8

| Sample | Parameters processed as one peak | | | | Parameters processed as two peaks | | | |
|---|---|---|---|---|---|---|---|---|
| | $M_{wt}$[1] | % by Mass | P | Rg | $M_{wt}$ | % by Mass | P | Rg |
| 5 | $8.05 \pm 0.44 \times 10^5$ | 99 | 2.48 | 34.1 | $3.20 \pm 0.18 \times 10^6$ | 13.6[2] | 1.55 | 49.7 |
| | | | | | $3.95 \pm 0.04 \times 10^5$ | 85.5 | 1.39 | — |
| 5/24 | $1.63 \pm 0.28 \times 10^6$ | 107 | 4.73 | 124 | $5.88 \pm 1.1 \times 10^6$ | 23.4[2] | 2.43 | 138 |
| | | | | | $4.06 \pm 0.32 \times 10^5$ | 84.5 | 1.48 | 21 |

[1] Weight average molecular weight of the gum arabic sample
[2] Arabinogalactan protein content of the gum arabic sample (% by weight)

TABLE 9

| Sample | Parameters processed as one peak | | | | Parameters processed as two peaks | | | |
|---|---|---|---|---|---|---|---|---|
| | $M_{wt}$[1] | % by Mass | P | Rg | $M_{wt}$ | % by Mass | P | Rg |
| 6 | $1.65 \pm 0.66 \times 10^6$ | 105 | 1.77 | 27.1 | $4.82 \pm 0.19 \times 10^6$ | 15.77[2] | 1.20 | 30.5 |
| | | | | | $1.10 \pm 0.10 \times 10^6$ | 89.7 | 1.33 | 24.1 |
| 6/15 | $3.65 \pm 0.17 \times 10^6$ | 110 | 2.75 | 40.2 | $8.38 \pm 0.44 \times 10^6$ | 37.2[2] | 1.53 | 42.5 |
| | | | | | $1.21 \pm 0.04 \times 10^5$ | 73.2 | 1.26 | 30.7 |

[1] Weight average molecular weight of the gum arabic sample
[2] Arabinogalactan protein content of the gum arabic sample (% by weight)

Experimental Example 7

Spray-dried gum arabic (*A. seyal*: 'Sample 7') (powdered form: 2 mm or less) was heated at 110° C. for 24 hours using an oven (gum arabic heated for 24 hours is referred to as 'Sample 7/24') in the same manner as in Experimental Example 2. These gum arabic samples (Sample 7 and Sample 7/24) were subjected to GPC-MALLS and the chromatograms were obtained in the same manner as in Experimental Example 1. Various parameters (weight average molecular weight, recovery ratio (% mass), polydispersity (P) value, and RMS-radius of gyration (Rg)) were obtained by processing the obtained data in the same manner as in Experimental Example 1. The results are shown in Table 10.

TABLE 10

| | Parameters processed as one peak | | | | Parameters processed as two peaks | | | |
|---|---|---|---|---|---|---|---|---|
| Sample | $M_{wt}$[1] | % by Mass | P | Rg | $M_{wt}$ | % by Mass | P | Rg |
| 7 | $1.15 \pm 0.04 \times 10^6$ | 107 | 2.80 | 36.4 | $4.72 \pm 0.33 \times 10^6$ | $10.9^{2)}$ | 1.73 | 47.8 |
| | | | | | $5.85 \pm 0.14 \times 10^5$ | 96.7 | 1.56 | 13.2 |
| 7/24 | $1.46 \pm 0.26 \times 10^6$ | 104 | 3.13 | 51.5 | $6.15 \pm 0.57 \times 10^6$ | $22.9^{2)}$ | 1.81 | 60.3 |
| | | | | | $3.82 \pm 0.08 \times 10^5$ | 82 | 1.47 | 18.5 |

[1]Weight average molecular weight of the gum arabic sample
[2]Arabinogalactan protein content of the gum arabic sample (% by weight)

Experimental Example 8

Immune Reaction of Modified Gum Arabic

Immune-reactivity of each of gum arabic samples from *A. senegal* (Sample 3, Sample 3/24, and Sample 3/48) obtained in Experimental Example 3 were evaluated. More specifically, immune-reactivity of each of gum arabic samples was measured using plates immobilized with the each gum arabic (concentrations: 0.005, 0.01, 0.05, 0.1, 0.5, 1, 5 mg/ml) by indirect competitive ELISA according to Thurston, M. I. et al. [Thurston, M. I., et al., Detection of gum from *Acacia seyal* and species of combretum in mixtures with *A. senegal* using monoclonal antibodies, Food & Agric. Immunol., 10:237-241 (1998); Thurston, M. I., et al., Effect of heat and pH on carbohydrate epitopes from *Acacia senegal* by specific monoclonal antibodies, Food & Agric. Immunol., 11:145-153 (1999)]. The ELISA method is described below.

Monoclonal antibodies having no specificity to any species of gum arabic and showing quantitative cross-reactivity were prepared. More specifically, adjuvant was added to saline solution containing 1 mg/ml of gum arabic from *Acasia seyal* to prepare the immunogen. Balb/c mice were given intraperitoneal injections of the immunogen three times at 2-week intervals. The splenocytes of the mice with highly raised antibody titers were taken and fused with the myeloma cells in polyethylene glycol. After incubating the obtained cells on an incubation plate for 10 days, the hybridoma cells were selected based on specificity of antibodies produced in the supernatant of the proliferated hybridoma cells. The selected hybridoma cells were incubated for another 10 days on the incubation plate and specific hybridoma cells were selected by the same procedure. The hybridoma cells producing only SYCC7 antibodies having no specificity to any species of gum arabic and showing quantitative cross-reactivity were finally selected.

Each of 1 mg/ml and 5 mg/ml solutions of the three samples (Sample 3, Sample 3/24, and Sample 3/48) was diluted at 10-fold, 100-fold and 1000-fold. 200 μl of each solution was added into wells of a plastic plate, and immobilized at 4° C. for 1 hour. The wells were washed with saline solution, blocked with 0.3% casein-containing saline solution and washed with 0.05% Tween 20-containing saline solution. Culture supernatant of the prepared hybridoma cells was added and immobilized for 1 hour. After washing as in the above-mentioned procedure, the wells were subsequently immobilized with peroxidase-labeled goat anti-mouse antibodies (SIGMA, diluted 1,000-fold with saline solution) for 1 hour. After washing, tetramethylbenzidine was added as a substrate to the wells and the color intensity was measured as UV absorption at 450 nm ($UV_{450\ nm}$). The inhibition ratio (%) for each sample at various concentrations was indicated by comparison with the UV absorption at 450 nm ($UV_{450\ nm}$) of natural gum arabic from *A. seyal*, which is 100% inhibition.

Figure 5:
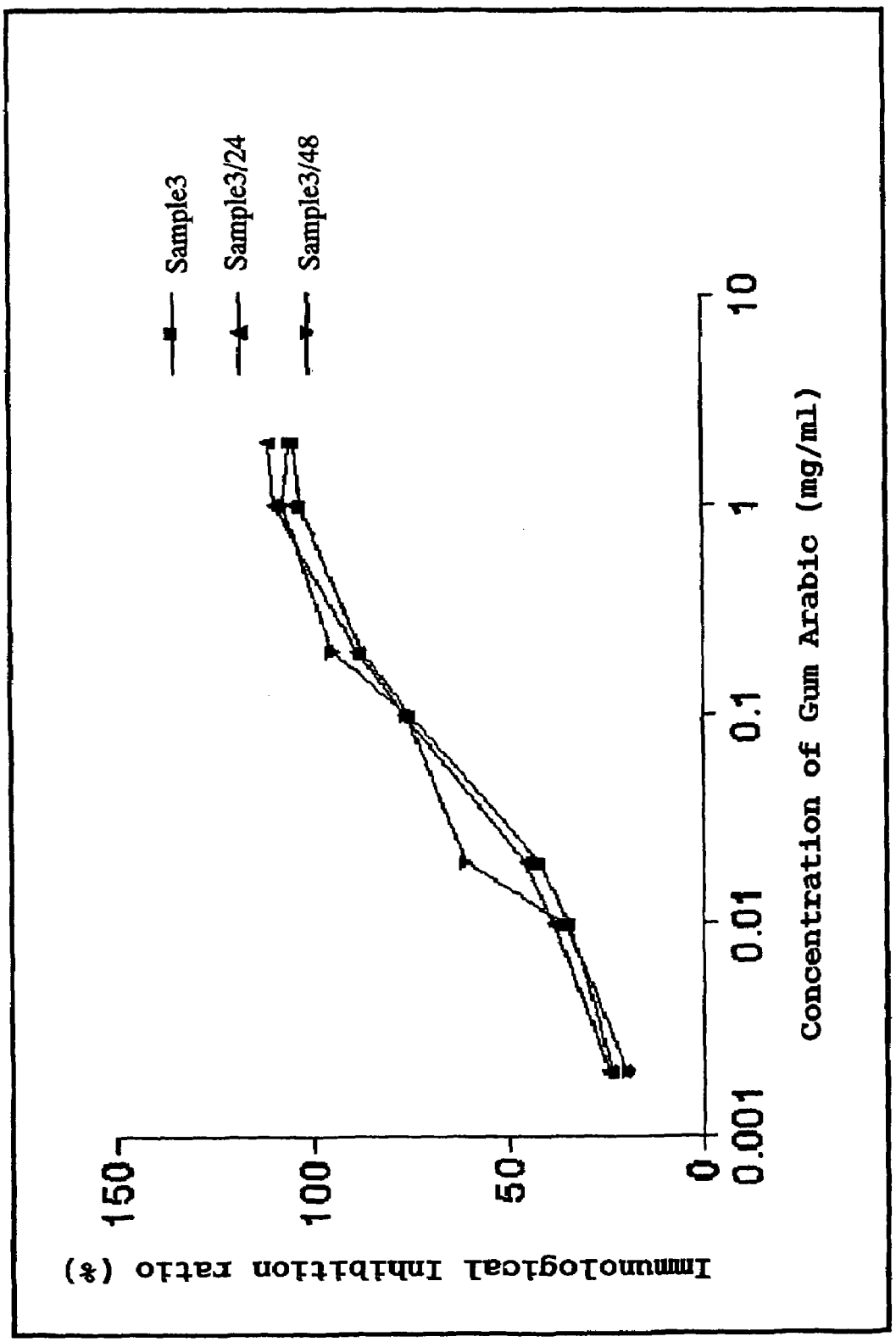
FIG. 5 shows the immunological inhibition ratio (%) obtained by conducting indirect competitive ELISA using quantifiable antibodies (SYCC7) for Sample 3, Sample 3/24, and Sample 3/48 in Experimental Example 8.

The results are shown in FIG. 5. The abscissa represents the concentration (mg/ml) of each gum arabic sample used for coating the plates, and ordinate represents the inhibition ratio (%). Test results show that the modified gum arabic of the present invention and natural gum arabic have the same or similar immunological reactivity since differences in the immunological inhibition ratio therebetween are within the range of ±10% over the tested concentrations, and therefore negligible.

Example 1

β-Carotene Emulsion (an Emulsified Colorant Preparation)

Using the heat-treated gum arabic samples (*Acacia senegal*) obtained in Experimental Examples 1 through 6 as modified gum arabic samples, β-Carotene emulsions were prepared according to the formulation given below.

| <Formulation> | |
|---|---|
| β-Carotene 30% suspension | 5 |
| Medium-chain triglyceride | 10 |
| Modified gum arabic (*Acacia senegal*) | 17 |
| Water | 68 |
| Total | 100 (% by weight) |

More specifically, 170 g of modified gum arabic (*Acasia Senegal*) was dissolved in 680 g of water, and the solution was centrifuged to remove insoluble substances, thus giving a 20% aqueous solution of modified gum arabic. The gum arabic solution was used as an emulsifier, and to the solution was added a mixed solution prepared by dissolving 100 g of medium-chain triglyceride (octanoic/decanoic acid triglyceride O.D.O (trade name, product of Nisshin Oil Mills, Ltd.)) in 50 g of a 30% suspension of β-carotene with heating at 150° C., followed by mixing under stirring. The mixture was emulsified with a homogenizer (manufactured by APV Gaulin) (homogenized 4 times at the pressure of 44 MPa (450 kg/cm$^2$)) to give a β-Carotene emulsion serving as an emulsified colorant preparation.

Example 2

Orange Flavoring Emulsion (an Emulsified Flavoring)

Using the heat-treated gum arabic samples (*Acacia senegal*) obtained in Experimental Examples 1 through 6 as modified gum arabic samples, orange flavoring emulsions were prepared according to the formulation given below.

<Formulation>

| | | |
|---|---|---|
| Orange flavoring | 2 | (% by weight) |
| Medium-chain triglyceride | 13 | |
| Modified gum arabic (*Acacia senegal*) | 17 | |
| Water | 68 | |
| Total | 100 | (% by weight) |

More specifically, 170 g of modified gum arabic (*Acasia senegal*) was dissolved in 680 g of water, and the solution was centrifuged to remove insoluble substances, thus giving a 20% aqueous solution of modified gum arabic. The gum arabic solution was used as an emulsifier, and to the solution was added a mixed solution prepared by sufficiently mixing 20 g of orange flavoring and 130 g of medium-chain triglyceride (octanoic/decanoic acid triglyceride O.D.O (trade name, product of Nisshin Oil Mills, Ltd.)) at room temperature, followed by mixing by stirring. The mixture was emulsified with a homogenizer (manufactured by APV Gaulin) (homogenized 4 times at the pressure of 44 MPa (450 kg/cm$^2$)) to give an orange flavoring emulsion serving as an emulsified flavoring.

Example 3

Docosahexaeoic Acid (DHA) Emulsion (an Emulsified DHA Preparation)

Using the heat-treated gum arabic samples (*Acacia senegal*) obtained in Experimental Examples 1 through 6 as modified gum arabic samples, DHA emulsions were prepared according to the formulation given below.

<Formulation>

| | | |
|---|---|---|
| 20% DHA containing fish oil | 5 | (% by weight) |
| Medium-chain triglyceride | 10 | |
| Modified gum arabic (*Acacia senegal*) | 17 | |
| Water | 68 | |
| Total | 100 | (% by weight) |

More specifically, 170 g of modified gum arabic (*Acasia senegal*) was dissolved in 680 g of water, and the solution was centrifuged to remove insoluble substances, thus giving a 20% aqueous solution of modified gum arabic. The gum arabic solution was used as an emulsifier, and to the solution was added a mixed solution prepared by mixing 50 g of 20% DHA containing fish oil and 100 g of medium-chain triglyceride (octanoic/decanoic acid triglyceride O.D.O (trade name, product of Nisshin Oil Mills, Ltd.)) and heating the mixture at 80° C., followed by mixing by stirring. The mixture was emulsified with a homogenizer (manufactured by APV Gaulin) (homogenized 4 times at the pressure of 44 MPa (450 kg/cm$^2$) ) to give a DHA emulsion.

Example 4

Lemon Powder Flavoring

Using the heat-treated gum arabic sample (*Acacia seyal*) obtained in Experimental Example 7 as a modified gum arabic sample, a lemon powder flavoring was prepared according to the formulation given below.

<Formulation>

| | | |
|---|---|---|
| Lemon oil | 20 | (% by weight) |
| Modified gum arabic (*Acacia seyal*) | 20 | |
| Dextrin | 60 | |
| Water | 150 | |
| Total | 250 | (% by weight) |

More specifically, 200 g of the modified gum arabic (*Acasia seyal*) and 600 g of dextrin was dissolved in 1,500 g of water to prepare an aqueous solution of modified gum arabic. The gum arabic solution was used as an emulsifier. Lemon oil (200 g) was added to the gum arabic solution, followed by mixing by stirring. The obtained mixture was emulsified with a homogenizer (manufactured by APV Gaulin) (homogenized once at the pressure of 19.6 MPa (200 kg/cm$^2$)). Subsequently, the solution was spray-dried with a spray dryer (manufactured by Anhydro) (inlet temperature 140° C., outlet temperature 80° C.), to prepare a lemon powder flavoring (950 g).

INDUSTRIAL APPLICABILITY

The present invention can provide a modified gum arabic, especially a modified gum arabic from the species *A. senegal*, with improved emulsifiability. Moreover, the present invention can provide a modified gum arabic, especially a modified gum arabic from the species *A. senegal*, which exhibits stable and improved emulsifiability by uniformly adjusting and standardizing, especially in terms of emulsifiability variations in quality and properties of natural gum arabic ascribable to different harvesting areas, times and climates. Such a modified gum arabic of the invention, especially a modified gum arabic from the species *A. senegal*, can be suitably used for emulsifying various hydrophobes such as essential oils, oil-based colorants, oil-based flavorings, oil-soluble vitamins, etc. The emulsions prepared using the modified gum arabic of the invention are more stable in quality as compared with those prepared using natural (unmodified) gum arabic since particle distribution is uniform and qualitative deterioration caused by agglomeration or integration of the emulsion particles under conditions such as heating or long-time storage can be significantly suppressed.

The present invention can provide a modified gum arabic, especially a modified gum arabic from the species *A. seyal*, with improved and enhanced emulsifiability, emulsion stability, encapsulation ability, adhesiveness, protective colloid property, and filmforming ability as compared with natural (unmodified) gum arabic. Moreover, the invention can provide a modified gum arabic, especially a modified gum arabic from the species from *A. seyal*, which exhibits stable emulsifiability by uniformly adjusting and standardizing variations in quality and properties of gum arabic ascribable to different harvesting areas, times climates, especially in terms of emulsifiability, encapsulation ability, adhesiveness, protective colloid property, filmforming ability, etc. Such a modified gum arabic of the invention can be suitably used for a thickener, binder, material for capsules (encapsulant), coating agent and emulsifier.

The invention claimed is:

1. A water-soluble modified gum arabic from acacia senegal, having an RMS-radius of gyration of arabinogalactan protein of 42.3 to 138 nm; and having at least one of the following characteristics: (a) a weight-average molecular weight of not less than 1.5 million Da and (b) an arabinogalactan protein content of not less than 17 weight %.

2. A water-soluble modified gum arabic according to claim 1, wherein the weight average molecular weight is not less than 2 million Da.

3. A water-soluble modified gum arabic according to claim 1, wherein the difference in the degree of immunological inhibition between the modified gum arabic and the unmodified starting gum arabic is within ±10% as measured by indirect competitive ELISA using a quantifiable antibody for gum arabic.

4. A water-soluble modified gum arabic according to claim 1, wherein the difference between the average droplet particle diameter in the emulsion immediately after emulsification and after 2 to 7 days storage at 60° C. is less than 0.1 µm, when the water-soluble modified gum arabic is emulsified with medium-chain triglyceride by stirring a mixture of medium-chain triglyceride and 20% aqueous solution of the water-soluble modified gum arabic, where a ratio of said medium-chain triglyceride to said 20% aqueous solution of the water-soluble modified gum arabic being 15:85 or 20:80 by weight.

5. An emulsifier comprising the modified gum arabic of any one of claims 1, 2, 3 and 4 as an active component.

6. A stabilized emulsion comprising a dispersion of a hydrophobic substance in a hydrophilic solvent in the emulsifier of claim 5.

7. The emulsion according to claim 6, which is an oil/water emulsion or a water/oil/water emulsion.

8. The emulsion according to claim 6, wherein the hydrophobic substance is an edible hydrophobic substance.

9. The emulsion according to claim 6, wherein the hydrophobic substance is at least one selected from the group consisting of essential oils, oleoresin, absolutes, oil-based flavorings, oil-based colorants, oil-soluble vitamins, $C_{18}$-$C_{22}$ polybasic unsaturated fatty acids, animal and vegetable fats and oils, SAIB and $C_6$-$C_{12}$ fatty-acid triglycerides.

10. A method for preparing an emulsion comprising mixing a hydrophobic substance and hydrophilic solvent in the presence of the emulsifier according to claim 5.

11. A thickener, coating agent, binder and material for capsules comprising the modified gum arabic according to any one of claims 1, 2, 3 and 4 as an active component.

* * * * *